United States Patent [19]
Jones et al.

[11] Patent Number: 5,903,685
[45] Date of Patent: May 11, 1999

[54] SENSOR ARRANGEMENT

[75] Inventors: Julian D. Jones; David C. Bownass; James S. Barton, all of Edinburgh, United Kingdom

[73] Assignee: British Telecommunications public limited company, London, United Kingdom

[21] Appl. No.: 08/675,818

[22] Filed: Jul. 5, 1996

[30] Foreign Application Priority Data

Nov. 29, 1995 [EP] European Pat. Off. .............. 95308586

[51] Int. Cl.$^6$ ...................................... G02B 6/26
[52] U.S. Cl. ............................ 385/12; 385/140; 385/145
[58] Field of Search ................................. 385/12, 31, 39, 385/30, 140, 145; 356/361, 73.1

[56] References Cited

U.S. PATENT DOCUMENTS

| | | | |
|---|---|---|---|
| 4,536,058 | 8/1985 | Shaw et al. | 350/96.15 |
| 4,788,436 | 11/1988 | Koechner | 350/96.34 |
| 4,846,548 | 7/1989 | Klainer | 350/96.29 |
| 5,136,818 | 8/1992 | Bramson | 356/73.1 |
| 5,343,037 | 8/1994 | Berkcan | 250/227.21 |

FOREIGN PATENT DOCUMENTS

| | | |
|---|---|---|
| 3922430 | 1/1991 | Germany . |
| 2210685 | 6/1989 | United Kingdom . |

OTHER PUBLICATIONS

Patent Abstracts of Japan, vol. 011, No. 311 (P–625), Oct. 12 1987 & JP–A–62 102139 (Cannon, Inc.), May 12 1987, *Abstract*.

Patent Abstracts of Japan, vol. 016, No. 504 (P–1439), Oct. 19 1992 & JP–A–04 184149 (Sumitomo Electric Ind Ltd.), Jul. 1 1992, *Abstract* & Database WPI Section Ch, Week 9233 Derwent Publications Ltd., London, GB; Class 004, AN 92–272164 *Abstract*.

Sensors and Actuators A, vol. A23, No. 1/3, Apr. 1 1990, pp. 1092–1096, XP000355779 Poscio P et al.: "Realization of a Miniaturized Optical Sensor for Biomedical Applications" * The Whole Document*.

Patent Abstracts of Japan, vol. 018, No. 532 (P–1810), Oct. 7 1994 & JP–A–096 186443 (Furukawa Electric Co Ltd), Jul. 8 1994, *Abstract* & Database WPI Section Ch, Week 9432 Derwent Publications Ltd., London, GB; Class 004, AN 94–257634 *Abstract*.

*Primary Examiner*—Hung N. Ngo
*Attorney, Agent, or Firm*—Nixon & Vanderhye P.C.

[57] ABSTRACT

A substance sensor comprises a single-mode optical fibre having a core and a cladding having a lower refractive index than that of the core. A sensor material extends within the cladding towards the core. A layer of cladding is left between the sensor material and the core. The thickness (t) of the layer is sufficiently small that the sensor material lies within the evanescent wave which occurs within the cladding when optical radiation is conducted through the core. The refractive index of the sensor material varies in the presence of a substance to be sensed over a range which extends above and below the refractive index of the cladding. When its refractive index is lower than that of the cladding the sensor material operates, as far as the radiation is concerned, similarly to the cladding. However, when the refractive index of the sensor material is higher than that of the cladding the sensor material couples out some of the radiation, thereby reducing the transmissivity of the fibre. The sensor material may be, for example, polyethylene oxide, in which case the arrangement operates as a humidity sensor.

19 Claims, 2 Drawing Sheets

SENSOR ARRANGEMENT

BACKGROUND OF THE INVENTION

1. Field of the Invention

This invention relates to a sensor arrangement comprising an optical waveguide having a core of material which is transmissive for optical radiation having a given wavelength and a cladding which surrounds the core, the cladding being of material which has a refractive index at the given wavelength which is less than the refractive index of the adjacent surface of the core, the arrangement including a sensor material which is capable of taking up a given substance or substances within itself and has a refractive index which is dependent upon the amount of such substance(s) taken up, the sensor material being positioned sufficiently close to the core as to be capable, at least when the refractive index of the sensor material has a first value corresponding to a first said amount of substance(s) taken up, of coupling radiation having the given wavelength out from the core and thereby reducing the transmissivity of the waveguide for radiation having the given wavelength.

2. Related Art

An arrangement of this general kind is known, for example, from U.S. Pat. No. 4,634,856. The known arrangement is for sensing moisture and comprises an optical fibre core surrounded by cladding material. The cladding material has a refractive index which is a function of its moisture content and may be constituted by sintered or porous plastic. In this known arrangement the sensor material and the cladding material are therefore one and the same. It appears that the refractive index of the dry plastic is less than that of water and that the effective refractive index increases towards that of the core with increasing moisture content. Light signals are transmitted through the fibre from a light source at one end to a detector unit at the other. The increase in the refractive index of the cladding towards that of the core occurring with increasing moisture content results in a modification of the modal power distribution in the core and hence in attenuation of the light signals received by the detector unit. It appears that, for this to occur, the fibre operates as a multimode waveguide. The specification mentions that information on optical signal loss throughout the length of the fibre can be obtained by means of an optical time-domain reflectometer (OTDR). Thus moisture content can be measured at any point along the entire length of an elongated optical fibre arranged about or along a substantial area being monitored. Moisture measurements can be made at many points along a single optical fibre cable containing numerous individual optical fibres for monitoring at the desired locations.

Single-mode optical fibres are being increasingly employed to carry signals in telecommunications networks. Multi-fibre cables are conventionally used, couplings being made to individual fibres at convenient "splitter" nodes. Because the operation of these nodes tends to be degraded by moisture, steps have to be taken to minimise this risk, for example by hermetically sealing the nodes and packing them with silica gel. Even so there is still a finite risk of the relative humidity within the nodes rising to an unacceptable level. If this should occur it is highly desirable that the situation be detected promptly, so that remedial action can be taken before unacceptable degradation occurs.

It is of course possible to provide one of the many known humidity sensors in each node and interrogate it, and power it also if necessary, from a central monitoring point by means of electrical wiring. However this is cumbersome and costly and there is a need for a humidity sensor which can be included in, and monitored via, a length of single-mode optical fibre. Preferably too it should be possible to construct such a sensor in such a way that it does not result in an unacceptably large attenuation of signals passing through the fibre, whatever the ambient humidity is, so that several such sensors can be included at successive locations along the same fibre and be satisfactorily monitored via that fibre.

SUMMARY OF THE INVENTION

It is an object of the invention to enable the above needs to be met.

According to the invention a sensor is characterised in that the sensor material extends within the cladding material towards the core but is separated from the core by cladding material, and in that the cladding material has a refractive index at the given wavelength which is intermediate a first refractive index of the sensor material and a second refractive index of the sensor material said second refractive index corresponding to a second amount of substance(s) taken up in the sensor material.

As the sensor material is separated from the core by cladding material the insertion loss of the arrangement for radiation transmitted through the core can be small when the second refractive index of the sensor material has the second value. Moreover, the insertion loss when the first of the sensor material has the first value can be tailored to particular circumstances by suitably choosing the separation between the sensor material and the core.

Preferably the optical waveguide is a single-mode optical waveguide at the given wavelength.

If the arrangement is required to operate as a humidity sensor arrangement the sensor material may suitably be a hydrophilic polymer, for example polyethylene oxide.

In order to facilitate construction, the optical waveguide may be an optical fibre which is embedded in a block of material having a flat surface, the surface of a thinned portion of the cladding forming part of the flat surface and the sensor material being present as a layer on the flat surface.

BRIEF DESCRIPTION OF THE DRAWINGS

Embodiments of the invention will now be described, by way of example, with reference to the accompanying drawings in which.

DETAILED DESCRIPTION OF EXEMPLARY EMBODIMENTS

Figure 1:
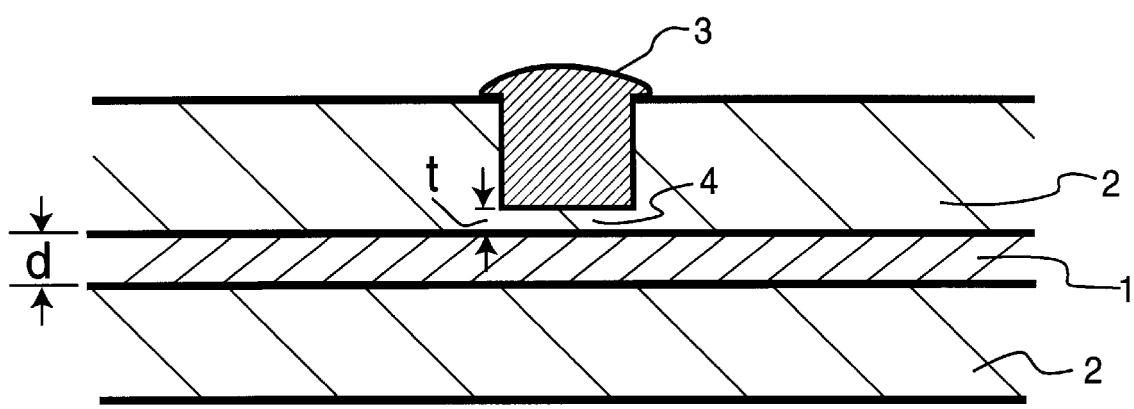
FIG. 1 shows a longitudinal section through a first embodiment.

FIG. 1 is a section, taken in the length direction, through an optical waveguide in the form of an optical fibre having a core 1 surrounded by a cladding 2. The core 1 may, for example, carry optical signals from an Optical Time Domain Reflectometer (not shown). In usual fashion the refractive index $N_1$ of the core 1 is higher than the refractive index $N_2$ of the cladding 2 at the wavelength(s) of the optical signals, so that the signals are guided by the core 1. The core 1 can be circular in cross-section and its diameter d is preferably sufficiently small that the waveguide is a single-mode waveguide at the wavelength(s) of the optical signals.

The section of waveguide shown operates as a humidity sensor. To this end a sensor material 3 extends within the conventional cladding 2 towards the core 1. The sensor material 3 is capable of taking up water vapour within itself and its refractive index $N_3$ is, at least at the wavelength(s) of the signals carried by the core 1, dependent upon the amount of water vapour taken up. More particularly, as the concentration of water in the material 3 increases, the refractive index $N_3$ moves through a range of values which includes the refractive index $N_2$ of the cladding material so that, at a particular concentration, $N_3=N_2$.

The material 3 extends from the exterior towards the core 1 but is spaced from the material of the core by a thin layer 4 of the cladding material 2. The thickness t of this layer, i.e. the spacing between the material 3 and the core 1, is sufficiently small that the portion of the material 3 adjacent the core lies within the evanescent waves created in the cladding 2 by the optical signals carried by the core 1. At concentrations of water in the material 3 at which its refractive index $N_3$ is equal to or less than the refractive index $N_2$ of the cladding material 2 the material 3 behaves in a similar way to the cladding material 2 as far as the signals carried by the core 1 are concerned. However, at concentrations of water at which $N_3$ is greater than $N_2$ the material 3 couples out some of the signal energy from the core 1 and thereby reduces the transmissivity of the waveguide. This reduction in transmissivity can be sensed, for example, by means of an optical radiation detector (not shown) positioned at one end of the waveguide to receive optical radiation transmitted by the waveguide from a source (also not shown) positioned at the other end, or by means of an Optical Time Domain Reflectometer positioned at one end of the waveguide to transmit optical radiation pulses into the waveguide and detect the reflections of this radiation caused by the coupling out of energy by the material 3.

The amount of energy coupled out by the material 3 at water concentrations at which its refractive index is higher than that of the cladding material 2 is highly dependent on the thickness t of the layer 4. Thus the reduction in the transmissivity of the waveguide 1,2 which occurs at these concentrations can be chosen to suit particular circumstances by suitably choosing the thickness t. For example, if only a single sensor as shown in FIG. 1 is provided along a given optical fibre it may be appropriate to choose the reduction in transmissivity to be large, i.e. to choose a very small value of t, so as to achieve maximum sensitivity. On the other hand, if several such sensors are provided at successive locations along the same fibre a large reduction in transmissivity caused by one sensor is likely to hinder the monitoring, via the fibre, of the others. In such a situation it may be appropriate to choose a relatively small reduction in transmissivity, i.e. to choose a relatively large value of t.

It will be noted from FIG. 1 that the cladding 2 is, at the region where it adjoins the core 1, continuous along the length of the waveguide or fibre. This enables the loss caused by the presence of the sensor material 3 to be kept very low in situations where the refractive index of the sensor material 3 is equal to or lower than that of the cladding material 2.

Figure 2:
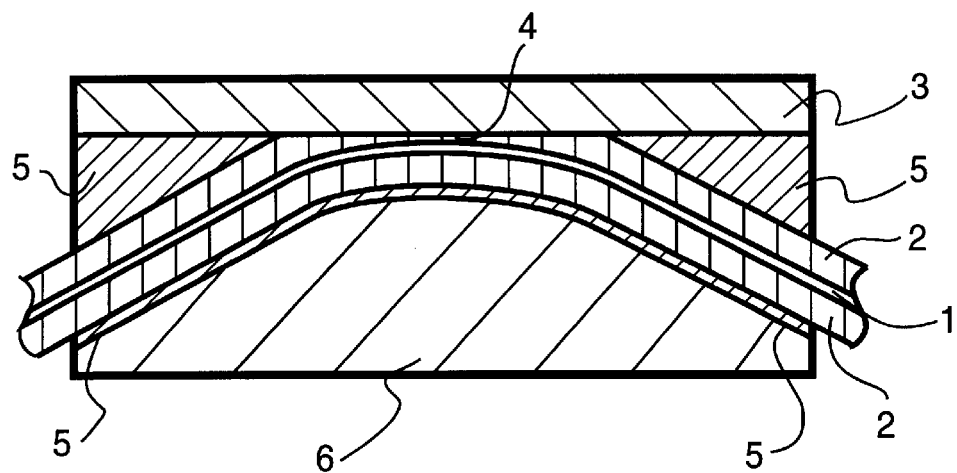
FIG. 2 shows a longitudinal section through a second embodiment.
Figure 3:
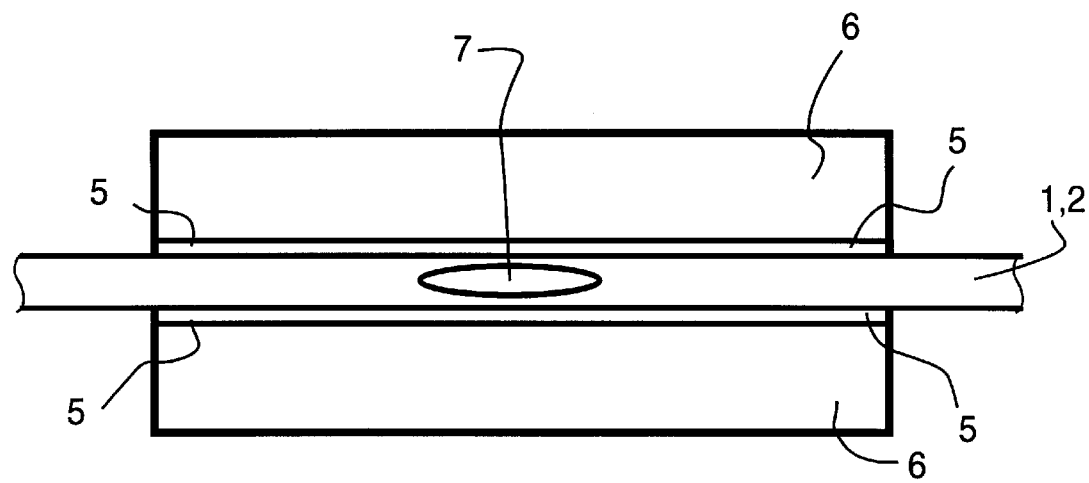
FIG. 3 is a plan view of part of the embodiment of FIG. 2.

The configuration shown in FIG. 1 is somewhat impractical to construct, and a preferred configuration will now be described with reference to FIGS. 2 and 3 of the drawings. In FIGS. 2 and 3 items which have counterparts in FIG. 1 have been given the same reference numerals.

The sensor arrangement of FIGS. 2 and 3 is, similarly to FIG. 1, shown in longitudinal section in FIG. 2. This sensor arrangement again comprises an optical fibre having a core 1 and a cladding 2. However the fibre 1,2 is now held by means of an appropriate adhesive 5, for example heat-cured epoxy resin, in a groove cut in the top surface of a quartz block 6: see also the plan view of the arrangement, minus the sensor material 3, shown in FIG. 3. The groove deepens on going away from the centre of the block 6 towards its edges, so that the fibre 1,2 is curved rather than straight in this embodiment. (The curvature is greatly exaggerated in FIG. 2). The top surface of the assembly of the block 6, the adhesive 5 and the embedded fibre 1,2 has been polished so that a portion 7 of the cladding 2 of the fibre 1,2 in the centre of the block 6 has been removed to leave a much thinner layer 4 of cladding at this area. The polishing has been continued until the layer 4 has the required thickness; c.f. the discussion above with reference to FIG. 1 of the dependence of the coupled out energy on the thickness t of the layer 4. Once the desired thickness of the layer 4 has been achieved a layer of the sensor material 3 has been provided over the whole of the top surface of the assembly of the block 6, the fibre 1,2 and the adhesive 5. The material 3 thus again extends within the cladding material 2 towards the core 1 but is again separated from the core 1 by cladding material 2.

In one example of a sensor arrangement constructed and configured as described with reference to FIGS. 2 and 3 the material of the core 1 was fused silica doped with germania so that its refractive index was approximately 0.3% greater than that of the cladding 2 at a wavelength of 435 nm. Its diameter was 8 $\mu$m. The material of the cladding 2 was fused pure silica having a refractive index of 1.433 at a wavelength of 435 nm. Its radial thickness was 58.5 $\mu$m. The thickness of the sensor material 3 was at least enough to restore the original cladding thickness at the region 7; a thickness of 100 $\mu$m was found to be satisfactory. The radius of curvature of the fibre 1,2 was 25 cm. The dimensions of the quartz block 6 were 10×10×30 nm.

The sensor material 3 used was polyethylene oxide (PEO), which is highly hydrophilic and also reversible in its response to water vapour. It was brushed on to the top surface of the block 6/fibre 1,2/adhesive 5 assembly in dissolved form and allowed to dry. This material expands as it takes up water vapour and contracts as it gives up water vapour, causing its refractive index to fall and rise respectively. The relative humidity at which its refractive index became equal to that of the cladding material 2 was approximately 80% at room temperature. (This value can be changed if desired by doping the PEO with a suitable dopant, for example sodium fluoride).

The thickness of the layer 4 was chosen to be such that approximately 50% of single-mode optical radiation of a given wavelength carried by the fibre 1,2 was coupled out by the sensor material 3 in situations (relative humidities) in which the refractive index of the sensor material 3 was greater than that of the cladding material 2. (This figure of 50% occurred for a wavelength of 1.3 $\mu$m and increased with increasing wavelength due to the corresponding increase in the mode field diameter of the light in the fibre). This thickness of the layer 4 was achieved by carrying out the polishing of the top surface of the block 6/fibre 1,2/adhesive 5 assembly in stages, and testing the properties of the assembly after each stage. The test method employed was the so-called "liquid drop" method for details of which reference may be made to an article "Measurement of the Core Proximity in Polished Fibre Substrates and Couplers" by Digonnet et al in Optics Letters, 10 (1985) at pages 463–5. This method basically consists in measuring the loss of transmission in the fibre 1,2 when liquid of an appropriate refractive index (higher than that of the cladding) is applied to the exposed fibre.

Figure 4:
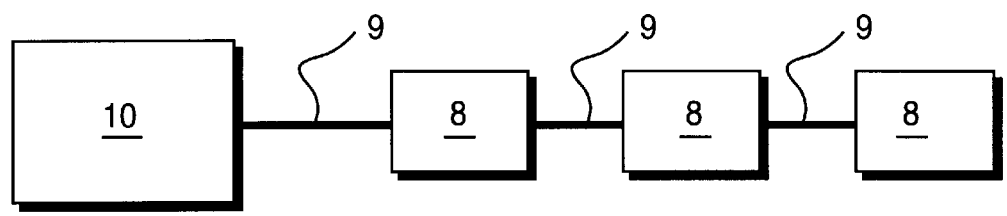
FIG. 4 shows a plurality of sensor arrangements included in succession within a single optical transmission path.

Several sensor arrangements, each as described with reference to FIGS. 2 and 3, may be included serially in a single optical fibre transmission path, as shown in FIG. 4. In FIG. 4 the sensor arrangements 8 are included serially in a single transmission path formed by a single-mode optical fibre 9. The fibre 9 is cut at each location where a sensor arrangement 8 is required and the two fibre ends thus created at each location are spliced to respective ends of the fibre 1,2 of that sensor arrangement. The arrangements 8 may be interrogated by means of an Optical Time Domain Reflectometer 10 positioned at one end of the fibre 9 for launching optical test signals into the fibre 9 and analysing signals received from the fibre 9 in response.

It will be evident that many modifications may be made to the embodiments described, while remaining within the scope of the invention as defined by the claims. For example the sensor material 3 may be something other than polyethylene oxide, for example gelatine. Indeed, sensor arrangements in accordance with the invention may be used to sense substances other than water vapour, if the sensor material 3 is chosen appropriately. In this last connection reference may be made, for example, to a paper by Ronot et al "Detection of chemical vapours with a specifically coated optical-fibre sensor" in Sensors and Actuators B, II (1993) pages 375–381 for a discussion of sensor materials whose refractive index varies in the presence of vapour of a given chemical or chemicals.

As a modification to the embodiments described a thin layer of a further material may be provided between the thin layer 4 of cladding material and the sensor material 3. In such a case the variation of the refractive index of the material 3 upon take up of the substance or substances to be sensed should be capable of encompassing a range which includes the refractive index of the further material rather than the refractive index of the cladding material.

While this invention has been described in conjunction with specific embodiments thereof, it is evident that many alternatives, modifications and variations will be apparent to those skilled in the art. Accordingly, the preferred embodiments of the invention, as set forth herein, are intended to be illustrative, not limiting. Various changes may be made without departing from the true spirit and full scope of the invention, as defined in the following claims.

We claim:

1. A sensor arrangement, comprising:
   an optical waveguide having a core of material which is transmissive for optical radiation having a predetermined wavelength;
   a cladding surrounding the core, the cladding comprising a material having a refractive index at said predetermined wavelength, which is less than a refractive index of an adjacent surface of the core;
   a sensor material capable of absorbing a given substance or substances to be detected and having a variable refractive index which is dependent upon an amount of said absorbed substance, the sensor material being positioned sufficiently close to the core, wherein when the refractive index of the sensor material has a value corresponding to a predetermined amount of substance(s) being absorbed, said sensor material couples radiation having the predetermined wavelength from the core, thereby reducing transmissivity of the waveguide for radiation having the predetermined wavelength, said sensor material extending into the cladding material towards the core, but remaining separated from the core by a predetermined thickness of said cladding material,
   wherein the sensor material is a hydrophilic polymer.

2. The sensor arrangement as claimed in claim 1, wherein the hydrophilic polymer comprises polyethylene oxide.

3. A sensor arrangement comprising:
   an optical waveguide having a core of material which is transmissive for optical radiation having a predetermined wavelength;
   a cladding surrounding the core, the cladding comprising a material having a refractive index at said predetermined wavelength, which is less than a refractive index of an adjacent surface of the core;
   a sensor material capable of absorbing a given substance or substances to be detected and having a variable refractive index which is dependent upon an amount of said absorbed substance, the sensor material being positioned sufficiently close to the core, wherein when the refractive index of the sensor material has a value corresponding to a predetermined amount of substance(s) being absorbed, said sensor material couples radiation having the predetermined wavelength from the core, thereby reducing transmissivity of the waveguide for radiation having the predetermined wavelength, said sensor material extending into the cladding material towards the core, but remaining separated from the core by a predetermined thickness of said cladding material,
   an optical time domain reflectometer coupled to the waveguide for transmitting optical radiation of the predetermined wavelength into the waveguide and receiving reflected radiation from the waveguide.

4. A sensor apparatus, comprising:
   a plurality of sensors disposed in series along an optical transmission path, said transmission path transmitting optical radiation at a predetermined wavelength, wherein each sensor of said plurality of sensors comprises:
   an optical waveguide having a core that is transmissive for optical radiation having said predetermined wavelength;
   a cladding surrounding said core, the cladding comprising a material having a refractive index at said predetermined wavelength that is less than a refractive index of said core; and
   a sensor material capable of absorbing a substance to be detected and having a variable refractive index dependent upon an amount of substance absorbed, said sensor material being disposed sufficiently close to said core wherein when the refractive index of said sensor material has a value corresponding to the refractive index of the core, the sensor material couples radiation of said predetermined wavelength, thereby effecting transmissivity of the core, the sensor material being isolated from the core by a predetermined thickness of said cladding.

5. The sensor arrangement, as claimed in claim 4 further comprising:
   an optical time domain reflectometer coupled to the transmission path for transmitting optical radiation of the predetermined wavelength into the transmission path and receiving reflected radiation from the transmission path.

6. The sensor apparatus as claimed in claim 4, wherein said cladding has a refractive index intermediate a range of refractive indices of said sensor material.

7. A humidity sensor apparatus, comprising:

an optical waveguide having a core of material that is transmissive for optical radiation having a predetermined wavelength;

a cladding surrounding said core and comprising a material having a refractive index that is lower than a refractive index of said core at said predetermined wavelength; and a hydrophilic polymer sensor material extending into said cladding, said sensor material being capable of absorbing water and having a variable refractive index that is dependent upon an amount of water absorbed by said sensor material, said sensor material being positioned sufficiently close to said core wherein when the refractive index of the sensor material has a value corresponding to a predetermined amount of water being absorbed, said sensor material couples radiation having said predetermined wavelength from said core, thereby reducing transmissivity of the waveguide for radiation having said predetermined wavelength, said sensor material being separated from the core by a predetermined thickness of the cladding material.

8. The humidity sensor apparatus of claim 7, wherein said cladding has a refractive index intermediate a range of refractive indices of said sensor material.

9. The humidity sensor apparatus of claim 7, wherein said optical waveguide comprises a single mode optical waveguide at said predetermined wavelength.

10. The humidity sensor apparatus of claim 7, wherein said hydrophilic polymer comprises polyethylene oxide.

11. The humidity sensor apparatus of claim 7, wherein said optical waveguide comprises an optical fiber embedded in a block of material having a flat surface, wherein a surface of a thinned portion of said cladding material forms part of said flat surface, said sensor material being disposed a layer on said flat surface.

12. The humidity sensor apparatus of claim 11, wherein said layer of sensor material has a thickness of at least 100 microns.

13. A humidity sensor apparatus, comprising:

a plurality of sensors disposed in series along an optical transmission path, said transmission path transmitting optical radiation at a predetermined wavelength, wherein each sensor of said plurality of sensors comprises:

an optical waveguide having a core of material that is transmissive for optical radiation having said predetermined wavelength;

a cladding surrounding said core and comprising a material having a refractive index that is lower than a refractive index of said core at said predetermined wavelength; and a hydrophilic polymer sensor material extending into said cladding, said sensor material being capable of absorbing water and having a variable refractive index that is dependent upon an amount of water absorbed by said sensor material, said sensor material being positioned sufficiently close to said core wherein when the refractive index of the sensor material has a value corresponding to a predetermined amount of water being absorbed, said sensor material couples radiation having said predetermined wavelength from said core, thereby reducing transmissivity of the waveguide for radiation having said predetermined wavelength, said sensor material being separated from the core by a predetermined thickness of the cladding material.

14. The humidity sensor apparatus of claim 13, further comprising an optical time domain reflectometer coupled to said transmission path, said reflectometer transmitting optical radiation of said predetermined wavelength into said transmission path and receiving backscattered radiation of said predetermined wavelength from said transmission path.

15. A sensor device, comprising:

an optical waveguide having a core of material, said core having a first index of refraction;

a cladding surrounding said core, said cladding having a second index of refraction; and a sensor material embedded in said cladding, said sensor material having a variable index of refraction, said variable index of refraction having a range extending above and below said second index of refraction.

16. The sensor device of claim 15, wherein said variable index of refraction of said sensor material is dependent upon an amount of substance to be detected by said sensor material.

17. The sensor device of claim 15, wherein said sensor material is capable of absorbing a substance to be detected and said variable index of refraction has a value dependent upon an amount of said substance being absorbed.

18. The sensor device of claim 17, wherein said substance is water.

19. The sensor device of claim 15, wherein said sensor material has a length that is less than a length of said cladding.

* * * * *